(12) United States Patent
Luo et al.

(10) Patent No.: US 11,148,986 B1
(45) Date of Patent: Oct. 19, 2021

(54) METHOD FOR EXTRACTING POLYOL FROM A FERMENTATION PROCESS (71) Applicant: SUZHOU SUZHEN BIOENGINEERING CO., LTD, Suzhou (CN)

(72) Inventors: Ji An Luo, Suzhou (CN); Guozhu Shi, Suzhou (CN); Yun Zhang, Suzhou (CN); Bin Liu, Suzhou (CN); Juanjuan Qian, Suzhou (CN); Juan Ding, Suzhou (CN); Wei Wang, Suzhou (CN); Wei Ji, Suzhou (CN)

(73) Assignee: SUZHOU SUZHEN BIOENGINEERING CO., LTD, Suzhou (CN)

( * ) Notice: Subject to any disclaimer, the term of this patent is extended or adjusted under 35 U.S.C. 154(b) by 0 days.

(21) Appl. No.: 17/271,597

(22) PCT Filed: May 7, 2020

(86) PCT No.: PCT/CN2020/088894
§ 371 (c)(1),
(2) Date: Feb. 26, 2021

(30) Foreign Application Priority Data

Apr. 29, 2020 (CN) .......................... 202010356220.3

(51) Int. Cl.
C07C 29/78 (2006.01)
C12P 7/00 (2006.01)
C12P 7/18 (2006.01)
C07C 29/76 (2006.01)

(52) U.S. Cl.
CPC .............. *C07C 29/78* (2013.01); *C07C 29/76* (2013.01); *C12P 7/18* (2013.01)

(58) Field of Classification Search
CPC .................................. C07C 29/78; C12P 7/18
See application file for complete search history.

(56) References Cited

FOREIGN PATENT DOCUMENTS

| CN | 101351252 A | 1/2009 |
| CN | 106748648 A | 5/2017 |
| CN | 109096052 A | 12/2018 |
| CN | 110922300 A | 3/2020 |
| PL | 224627 B1 | 1/2017 |
| PL | 224628 B1 | 1/2017 |

*Primary Examiner* — Sikarl A Witherspoon
(74) *Attorney, Agent, or Firm* — Bayramoglu Law Offices LLC (57) ABSTRACT A method for extracting polyol from a fermentation process is disclosed. The preparing method includes rectifying and purifying PDO (1,3-propanediol) from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is 99.5%. The preparing method meets the requirements of water resources recycling, reduces the production loss of PDO and BDO (2,3-butanediol) during the concentration, and greatly cuts down on the amount of wastewater.

23 Claims, 3 Drawing Sheets

METHOD FOR EXTRACTING POLYOL FROM A FERMENTATION PROCESS

CROSS REFERENCE TO THE RELATED APPLICATIONS

This application is the national phase entry of International Application No. PCT/CN2020/088894, filed on May 7, 2020, which is based upon and claims priority to Chinese Patent Application No. 202010356220.3, filed on Apr. 29, 2020, the entire contents of which are incorporated herein by reference.

TECHNICAL FIELD

The present invention belongs to the field of PDO biological preparation, and more particularly, relates to a method for extracting polyol from a fermentation process.

BACKGROUND 1,3-propanediol (PDO) and 2,3-butanediol (BDO) are both important chemical materials, and PDO is the key material for synthesizing memory fiber polytrimethylene terephthalate (PTT). The biological PDO production technology has been monopolized by DuPont for a long time, making PTT fiber unable to be mass-produced.

As a chemical material, BDO can be directly used in a variety of industries, such as organic solvents, cosmetic raw materials, flavor additives, fuel additives, etc.

In the process of producing PDO and BDO from microbial fermentation, after sterilized and desalinated, the fermentation broth is usually concentrated to remove most of water. During the evaporative dehydration, a small amount of PDO and BDO products evaporate into the condensed water, wherein the concentrations of the PDO and the BDO in the steam condensate are 1-4 g/l and 2-8 g/l respectively, resulting in a decrease in product yield. Luo Ji'an uses the Aspen simulation software to simulate the relationship between the product loss and the operating pressure during evaporative dehydration of the PDO fermentation broth, and simulates the product loss when concentrated to different water contents. Under optimized conditions, the concentrated solution is concentrated to 30% water content, and the PDO loss rate is 2.27%. In this case, in the factories with annual production of 20,000 tons of PDO, the annual PDO loss during evaporative dehydration will be 454 tons, and the BDO loss is much worse as 1362 tons, whose economic value is more than 30 million yuan. If the recycling can be implemented, the economic benefits of the enterprise will be significantly improved. The conventional method to reduce product loss in the concentration process requires multi-effect distillation and evaporation, but its equipment investment and energy consumption are very high. Part of the fraction evaporated at the top of the multi-effect rectification tower will be condensed and then returned to the rectification tower for repeated rectification, which makes the energy consumption of rectification significantly higher than that of the multi-effect evaporation. In addition, there are packing or trays in the multi-effect rectification tower, which is more complicated than multi-effect evaporation, therefore the investment in multi-effect distillation equipment with the same production capacity is much higher than that of multi-effect evaporation.

The patent No. 201811010380.1 discloses a method for concentrating 1,3-propanediol fermentation broth, which will increase the yield of 1,3-propanediol by adding absorption towers after the evaporator, but the addition of the absorption liquid will increase the energy consumption of concentration. In addition, the loss rate of 1,3-propanediol in this invention can be reduced to as low as 0.9%, which is relatively large for enterprises.

The patent No. 200680049905.1 discloses a method for separating propylene glycol from aqueous compositions, which is to concentrate the propylene glycol-containing composition by multi-effect rectification, and the propylene glycol contained in evaporated water of multi-effect rectification will be concentrated and recycled through a reverse osmosis membrane. This process requires reflux at the top of the tower, with a reflux ratio of 0.12-0.25, which increases the energy consumption of evaporation. In addition, there are 7-8 trays in the rectification tower, which is relatively large in equipment investment.

In addition, since the steam condensate contains 1-4 g/l PDO and 2-8 g/l BDO, it obviously inhibits the growth of bacteria from the fermentation process if directly used as the fermentation ingredient, and the growth rate of bacteria slows down, causing low PDO fermentation.

SUMMARY

The primary object of the present invention is to overcome the inadequacies in the prior art, including the excessive loss of PDO and BDO in the current evaporative dehydration of fermentation broth, which significantly inhibits the growth of bacteria when the steam condensate produced by the evaporative dehydration is reused for fermentation and contains higher concentrations of PDO and BDO. This invention comprises that the polyol in the steam condensate is condensed and filtered to be removed, and the steam condensate removed polyol is reused for fermentation, which meets the requirements of water resources recycling, reduces the production loss of PDO and BDO during the concentration, greatly cuts down on the amount of wastewater, and improves economic benefits. The invention provides a method for extracting polyol from a fermentation process, which is specifically in a faster, more efficient way with a greatly decrease on the energy consumption.

To this end, the key technical points of the invention are as follows:

A method for extracting polyol from a fermentation process, which is characterized by rectifying and purifying PDO from a polyol fermentation broth after concentration to form a steam condensate, wherein the concentration is evaporative dehydration; and filtering the steam condensate through a reverse osmosis membrane to form a concentrated solution, wherein the retentate of the reverse osmosis flows back to the evaporative dehydration; wherein the water content of the concentrated solution after the evaporative dehydration is 5-25 wt %; wherein the yield of PDO is ≥99.5%.

The following preferred technology program is presented to give a detailed description for this invention.

In the preparing method for extracting polyol from a fermentation process, wherein the water content of the polyol fermentation broth is ≥80 wt %;

wherein the polyol fermentation broth is the PDO fermentation broth after sterilization by filtration, or the PDO fermentation broth after sterilization by filtration and after desalination.

wherein the sterilization by filtration is a sterilization by microfiltration membrane filtration, a sterilization by ultrafiltration, a sterilization by nanofiltration, or a combination thereof.

wherein the desalination is a concentrated crystallization desalination, an electrodialysis desalination, a chromatographic separation desalination, an ion exchange desalination, or a combination thereof.

wherein the desalination is a one-step desalination or a multi-step desalination.

wherein the multi-step desalination refers to two or more combined desalination. For example, after a concentrated crystallization desalination, the primary desalted solution will be performed on a chromatographic separation desalination. For another example, after a concentrated crystallization desalination, the primary desalted solution will be performed on an electrodialysis desalination, and the secondary desalted solution will be performed on an ion exchange desalination for the third desalination. The combined desalination takes advantages of various processes with high desalination rate and high product yield.

wherein the concentration is a one-step concentration or a stepwise concentration.

wherein the stepwise concentration is a two-step concentration or a three-step concentration.

wherein the two-step concentration comprises that: the concentrated solution is primary concentrated until the water content is 50-70 wt %; after 80-99 wt % salt is removed, the concentrated solution is secondary concentrated until the water content is 5-25 wt %.

wherein the three-step concentration comprises that: the concentrated solution is primary concentrated until the water content is 50-70 wt %; after 30-60 wt % salt is removed, the concentrated solution is secondary concentrated until the water content is 30-50 wt %; before the third step, the concentrated solution is desalted again until the total desalination rate is 80-99 wt %; then the concentrated solution is tertiary concentrated until the water content is 5-25 wt %.

In any of the above preparing method, wherein the concentration is a multi-effect evaporative concentration, an MVR evaporative concentration or a multi-effect rectification.

In the preparing method for extracting polyol from a fermentation process, wherein the multi-effect evaporative concentration refers to the steam of the former effect as the heat source of the latter effect, including a three-effect evaporation, a four-effect evaporation, a five-effect evaporation and a six-effect evaporation.

wherein the reverse osmosis is a one-stage reverse osmosis or a multi-stage reverse osmosis. In the reverse osmosis, the steam condensate containing polyol is filtered through a reverse osmosis membrane, and most of the polyol intercepted by the membrane become the retentate, while water and a small amount of the polyol passing through the membrane become the penetrant. If the polyol amount in the penetrant is high, it will be intercepted from the reverse osmosis again, which is called the second-stage reverse osmosis.

wherein the multi-stage reverse osmosis refers to two or more stages of reverse osmosis, which connects the reverse osmosis in series, and the retentate of the subsequent stage flows back to the previous stage while the retentate of the previous stage flows back to the evaporative dehydration.

wherein the multi-stage reverse osmosis refers to two or more stages of reverse osmosis, which connects the reverse osmosis in series. At the same time, the retentate of the first-stage reverse osmosis is further filtered through the second-stage reverse osmosis, while the penetrant of the first-stage and second-stage reverse osmosis flows out, and the retentate of the second-stage reverse osmosis flows back to the multi-effect evaporation for evaporative dehydration.

wherein the multi-stage reverse osmosis refers to two or more stages of reverse osmosis, which connects the reverse osmosis in series. At the same time, the retentate of the first-stage reverse osmosis is further filtered through the second-stage reverse osmosis, while the penetrant of the first-stage and second-stage reverse osmosis flows out; then the retentate of the second-stage reverse osmosis is further filtered through the third-stage reverse osmosis, and the retentate of the third-stage reverse osmosis flows back to the multi-effect evaporation for evaporative dehydration, while the penetrant of the third-stage reverse osmosis flows back to the raw material of the first-stage reverse osmosis.

wherein the multi-stage reverse osmosis refers to two or more stages of reverse osmosis, which connects the reverse osmosis in series. At the same time, the penetrant of the first-stage reverse osmosis is further filtered through the second-stage reverse osmosis, and the penetrant of the second-stage reverse osmosis flows out, while the retentate of the first-stage reverse osmosis is further filtered through the third-stage reverse osmosis, and the retentate of the third-stage reverse osmosis flows back to the multi-effect evaporation for evaporative dehydration; then the retentate of the second-stage reverse osmosis and the penetrant of the third-stage reverse osmosis flows back to the raw material of the first-stage reverse osmosis.

wherein the products of rectification and purification include PDO as well as BDO.

wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria.

wherein the permeate of the reverse osmosis can be reused as a fermentation ingredient, as cleaning water or for sewage treatment.

The present invention discloses a method for extracting polyol from a fermentation process, using a combination of multi-effect evaporation and rectification for dehydration. The multi-effect evaporation can remove about 94% of water in the fermentation broth while the rectification is used to remove the remaining 6% of water. According to operation conditions, the two processes are basically equal in the energy consumption, which means that removing the same weight of water consumes more energy from the rectification than from the multi-effect evaporation. However, if the multi-effect evaporation is used to further increase the dehydration amount, the product loss of polyol will significantly increase. In addition, during the process of removing 94% of the water in the fermentation broth, the multi-effect evaporation causes 2.27% loss of PDO and more loss of BDO due to its low boiling point. The steam condensate containing PDO and BDO is directly reused for fermentation, which obviously inhibits the growth of bacteria from the fermentation process.

According to the inadequacies, the present invention adopts a reverse osmosis filtration process, which obtains the steam condensate from the multi-effect evaporation, and filters the steam condensate through a reverse osmosis membrane. Most of PDO and BDO are intercepted by the reverse osmosis membrane to form the retentate, while water and a small amount of PDO and BDO passes through the membrane to form the penetrant. The retentate with increasing concentrations of PDO and BDO can be returned to the evaporative dehydration for extracting PDO and BDO; the penetrant can be used as a fermentation ingredient, as cleaning water or for sewage treatment, because the concentrations of PDO and BDO in the penetrant largely decrease, which basically has no adverse effects on the fermentation process. After the decreasing concentration of PDO and BDO in the penetrant, the concentration of COD (chemical oxygen demand) and the cost of sewage treatment are significantly reduced.

The further effect of the present invention is that the energy consumption of dehydrating the polyol fermentation broth can be reduced. Based on the implementation of the reverse osmosis filtration, the dehydration of the fermentation broth will be optimized as follows: a multi-effect evaporation can remove 94-99.5% of water in the fermentation broth while a rectification is used to remove the remaining 0.5-6% of water, which takes full advantages of low energy consumption of multi-effect evaporation and high energy consumption of rectification and dehydration, reduces the amount of rectification and dehydration, and reduces the energy consumption of the fermentation broth dehydration.

In the invention, the PDO and BDO fermentation broth after sterilization by filtration is evaporated and dehydrated by MVR evaporation or multi-effect rectification with evaporators as two-effect, three-effect, four-effect, five-effect or six-effect. Afterwards, the concentrated solution is further purified through the bottom of the rectification tower. The steam condensate from the condensation (including primary and secondary steam condensate) contains higher concentrations of PDO and BDO, therefore it is filtered through the reverse osmosis equipment. Most of PDO and BDO are intercepted by the membrane, while water and a small amount of PDO and BDO passes through the reverse osmosis membrane. The PDO and the BDO solution intercepted by the reverse osmosis membrane can be returned to the concentration for further evaporation and dehydration, and the penetrant filtered by the reverse osmosis membrane is reused for fermentation as ingredients, because the concentrations of PDO and BDO are extremely low, which will not affect the growth and metabolism of bacteria on the fermentation process. The COD of the penetrant is greatly reduced, which can be used as cleaning water for the membrane equipment in the workshop, or discharged to the wastewater treatment system.

After the reverse osmosis filtration, more than 50% of the PDO and more than 67% of the BDO in the steam condensate can be recycled due to being intercepted by the reverse osmosis membrane, while the penetrant is reused as a fermentation ingredient. After the fermentation, the PDO concentration can reach 92.62-100.94 g/l, which is equivalent to the fermentation of pure water. In addition, the penetrate can also be reused for cleaning ceramic membranes, nanofiltration membranes and electrodialysis equipment, or directly used for sewage treatment.

The present invention reuses water by filtering polyol of the steam condensate. The sterilized fermentation broth is evaporative dehydrated by multi-effect evaporation, MVR evaporation or multi-effect rectification to obtain the steam condense (including primary and secondary steam condensate), which is filtered through the reverse osmosis. Most of PDO and BDO are intercepted by the reverse osmosis membrane, while water and a small amount of PDO and BDO passes through the membrane to form the penetrant, which is used as a ingredient of fermentation base materials, as cleaning water of the membrane equipment in the workshop, or discharged to the wastewater treatment system. This method reduces the consumption of water, and the COD and discharge of wastewater.

Based on the implementation of this invention, the dehydration of the fermentation broth will be optimized as follows: a multi-effect evaporation can remove 94-99.5% of water in the fermentation broth while a rectification is used to remove the remaining 0.5-6% of water, which takes full advantages of low energy consumption of multi-effect evaporation and high energy consumption of rectification and dehydration, reduces the load of rectification and dehydration, and reduces the energy consumption of the fermentation broth dehydration.

Benefits:

1) The PDO and BDO in the steam condensate are reused through reverse osmosis filtration, which reduces the losses of PDO and BDO. During the evaporative dehydration of the fermentation broth, the losses of PDO and BDO are respectively reduced from 2-5% to 0.18%, and from 15-30% to 0.09%, which is a major progress in the production of PDO and BDO from a fermentation process, greatly improving the economic benefits;

2) The penetrant after filtering and removing PDO and BDO can be reused as as a fermentation ingredient, or as cleaning water of the membrane equipment in the workshop, greatly reducing the consumption of water, the COD and discharge of wastewater, and the cost of wastewater treatment, which is an important measure to build a resource-saving production enterprise;

3) The improvement of dehydration process reduces the cost of dehydrating fermentation broth;

4) The invention makes the yield of PDO and BDO in the fermentation broth dehydration is ≥99.5%. Therefore, in a PDO project of 20,000 annual output, the energy consumption of evaporating 1 ton of water is as low as 198-280 kwh, the investment in multi-effect evaporation, rectification tower and reverse osmosis equipment is about 16 million yuan, and the yield of PDO and BDO reaches 99.5% because of using multi-effect rectification for the evaporative dehydration of the fermentation broth. In comparison, the energy consumption of evaporating 1 ton of water in the regular way is expected to be as high as 367 kwh, and the investment in equipment will be more than 30 million yuan.

Among these Figures, 1 is the concentration, 1A is the primary concentration, 1B is the secondary concentration, 2 is the reverse osmosis, 2A is the first-stage reverse osmosis, 2B is the second-stage reverse osmosis, 2C is the third-stage reverse osmosis, 3 is the fermentation, 4 is the fermentation broth, 5 is the steam condensate (including primary and secondary steam condensate), 6 is the retentate of the reverse osmosis, 6A is the retentate of the first-stage reverse osmosis, 6B is the retentate of the second-stage reverse osmosis, 6C is the retentate of the third-stage reverse osmosis, 7 is the penetrant of the reverse osmosis, 7A is the penetrant of the first-stage reverse osmosis, 7B is the penetrant of the second-stage reverse osmosis, 7C is the penetrant of the third-stage reverse osmosis, 8 is the desalination, 8A is the primary desalination, 8B is the secondary desalination, 9 is the desalted solution, 9A is the primary desalted solution, 9B is the secondary desalted solution, 10 is the concentrated solution, 10A is the primary concentrated solution, 10B is the secondary concentrated solution.

DETAILED DESCRIPTION OF THE EMBODIMENTS

Based on above mentioned method, the following embodiments are carried out for further demonstration in the present invention. It is to be understood that these embodiments are only intended to illustrate the invention and are not intended to limit the scope of the invention. In addition, it should be understood that after reading the contents described in the present invention, those technical personnel in this field can make various changes or modifications to the invention, and these equivalent forms also fall within the scope of the claims attached to the application.

Example 1

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration, and after one-step desalination as the electrodialysis desalination; wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria;

wherein the concentration of the polyol fermentation broth is one-step concentration as the multi-effect evaporative concentration, which refers to the steam of the former effect as the heat source of the latter effect, including a three-effect evaporation, a four-effect evaporation, a five-effect evaporation and a six-effect evaporation;

wherein the reverse osmosis is one-stage reverse osmosis.

Figure 1:
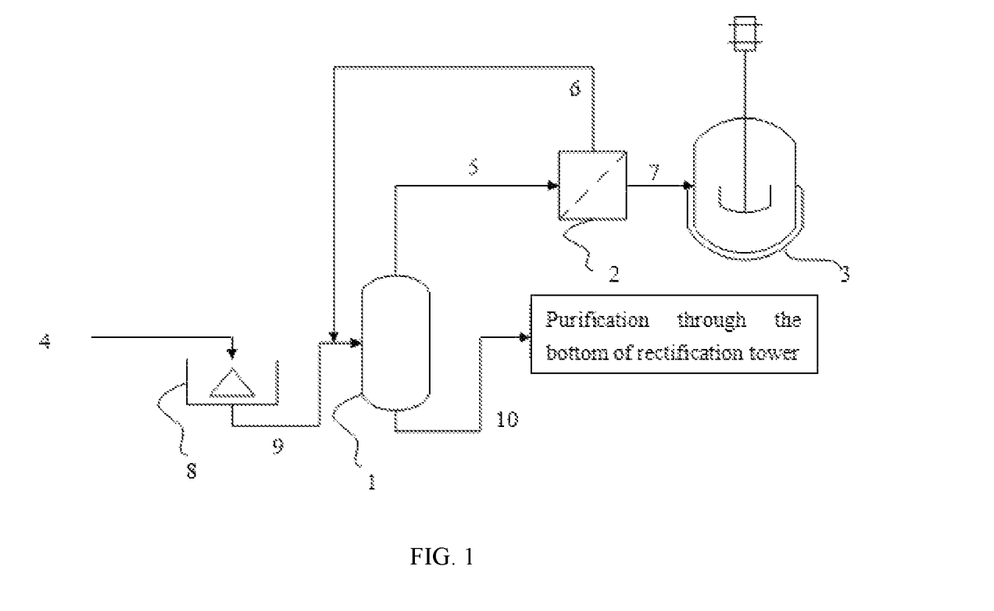
FIG. 1 is a flowchart of Example 1.

The process of a preparing method for extracting polyol from a fermentation process is shown in FIG. 1: the fermentation broth 4 for the desalination 8→the desalted solution 9 for the concentration 1→the concentrated solution 10 for purification through the bottom of the rectification tower while the steam condensate (including primary and secondary steam condensate) 5 for the reverse osmosis 2→the penetrant of the reverse osmosis 7 for the fermentation 3 while the retentate of the reverse osmosis 6 for the concentration 1.

Specifically, the polyol fermentation broth is dehydrated by the multi-effect evaporation, and the steam condensate (including primary and secondary steam condensate) is filtered by first-stage reverse osmosis, wherein the operating pressure of reverse osmosis is 2.5 MPa, the operating temperature is 35-36° C., the operating process is shown in FIG. 1, and the experimental data is shown in Table 1.

TABLE 1

Statistics of the multi-effect evaporation of fermentation broth and the reverse osmosis of condensate

| Materials | Mass (kg) | Water (g/l) | PDO (g/l) | BDO (g/l) | Glycerin (g/l) | Ethanol (g/l) |
|---|---|---|---|---|---|---|
| Polyol fermentation broth | 210 | 883.10 | 78.00 | 28.70 | 5.60 | 4.60 |
| Multi-effect evaporative steam condensate | 220 | 992.33 | 2.2 | 3.75 | 0 | 1.72 |
| Penetrant of reverse osmosis | 198 | 998.33 | 1.06 | 0.44 | 0 | 1.86 |
| Retentate of reverse osmosis | 22 | 956.59 | 12.25 | 28.02 | 0 | 3.14 |

Example 2

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration, and after one-step desalination as the electrodialysis desalination; wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria;

wherein the concentration of the polyol fermentation broth is one-step concentration as the MVR evaporative concentration;

wherein the reverse osmosis is two-stage reverse osmosis, which connects the reverse osmosis in series, and the retentate of the subsequent stage flows back to the previous stage while the retentate of the previous stage flows back to the evaporative dehydration.

Figure 2:
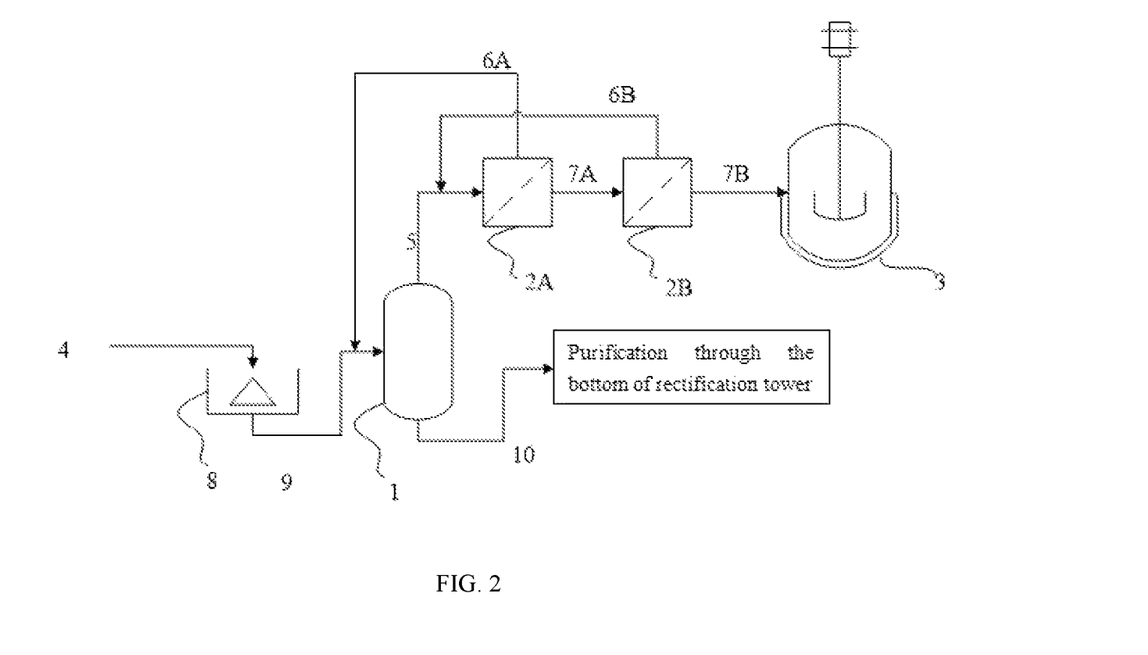
FIG. 2 is a flowchart of Example 2.

The process of a preparing method for extracting polyol from a fermentation process is shown in FIG. 2: the fermentation broth 4 for the desalination 8→the desalted solution 9 for the concentration 1→the concentrated solution 10 for purification through the bottom of the rectification tower while the steam condensate (including primary and secondary steam condensate) 5 for the first-stage reverse osmosis 2A→the penetrant of the first-stage reverse osmosis 7A for the second-stage reverse osmosis 2B while the retentate of the first-stage reverse osmosis 6A for the concentration 1→the penetrant of the second-stage reverse osmosis 7B for the fermentation 3 while the retentate of the second-stage reverse osmosis 6B for the first-stage reverse osmosis 2A.

Specifically, the polyol fermentation broth is dehydrated by the multi-effect evaporation, and the steam condensate (including primary and secondary steam condensate) is filtered by first-stage reverse osmosis, then filtered by second-stage reverse osmosis after the penetrant of the first-stage reverse osmosis is recycled, wherein the operating pressure of first-stage and second-stage reverse osmosis is 2.5 MPa, the operating temperature is 35-36° C., the operating process is shown in FIG. 2, and the experimental data is shown in Table 2.

TABLE 2

Statistics of the multi-effect evaporation of fermentation broth and the reverse osmosis of condensate

| Materials | Mass (kg) | Water (g/l) | PDO (g/l) | BDO (g/l) | Glycerin (g/l) | Ethanol (g/l) |
|---|---|---|---|---|---|---|
| Polyol fermentation broth | 252 | 882.10 | 77.20 | 29.30 | 6.20 | 5.20 |
| Multi-effect evaporative steam condensate | 272 | 996.8 | 3.18 | 7.95 | 0 | 3.74 |
| Retentate of first-stage reverse osmosis | 22 | 979.5 | 20.48 | 65.70 | 0 | 6.16 |
| Penetrant of first-stage reverse osmosis | 250 | 999 | 0.96 | 0.67 | 0 | 3.05 |
| Retentate of second-stage reverse osmosis | 22 | 992.8 | 7.18 | 5.39 | 0 | 8.34 |
| Penetrant of second-stage reverse osmosis | 228 | 999.9 | 0.15 | 0.03 | 0 | 2.19 |

The penetrant of reverse osmosis in Example 1 is used to prepare the fermentation base materials, including PDO 0.37 g/l, BDO 0.11 g/l and ethanol 1.31 g/l, whose fermentation level of PDO for 48 h fermentation is 100.94 g/l, and the bacteria concentration (650 nm absorbance value) is 14.96 for 24 h fermentation;

The penetrant of second-stage reverse osmosis in Example 2 is used to prepare the fermentation base materials, including PDO 0.17 g/l, BDO 0 g/l, and ethanol 4.26 g/l, whose fermentation level of PDO for 48 h fermentation is 92.62 g/l, and the bacteria concentration (650 nm absorbance value) is 14.94 for 24 h fermentation;

Pure water is used as a fermentation ingredient, whose fermentation level of PDO for 48 h fermentation is 94.32 g/l, and the bacterial concentration (650 nm absorbance value) is 13.42 for 24 h fermentation;

The multi-effect evaporative steam condensate in Example 1 is directly used as a fermentation ingredient. The fermentation base materials include PDO 2.2 g/l, BDO 3.75 g/l, and ethanol 1.72 g/l, whose fermentation level of PDO for 48 h fermentation is 85.36 g/l, and the bacteria concentration (650 nm absorbance value) is 12 for 24 h fermentation.

Example 3

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration, and after one-step desalination as the chromatographic desalination; wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria;

wherein the concentration of the polyol fermentation broth is one-step concentration as the multi-effect rectification;

wherein the reverse osmosis is two-stage reverse osmosis, which connects the reverse osmosis in series, and the retentate of the first-stage reverse osmosis is further filtered through the second-stage reverse osmosis, while the penetrant of the first-stage and second-stage reverse osmosis flows out, and the retentate of the second-stage reverse osmosis flows back to the multi-effect evaporation for evaporative dehydration.

Figure 3:
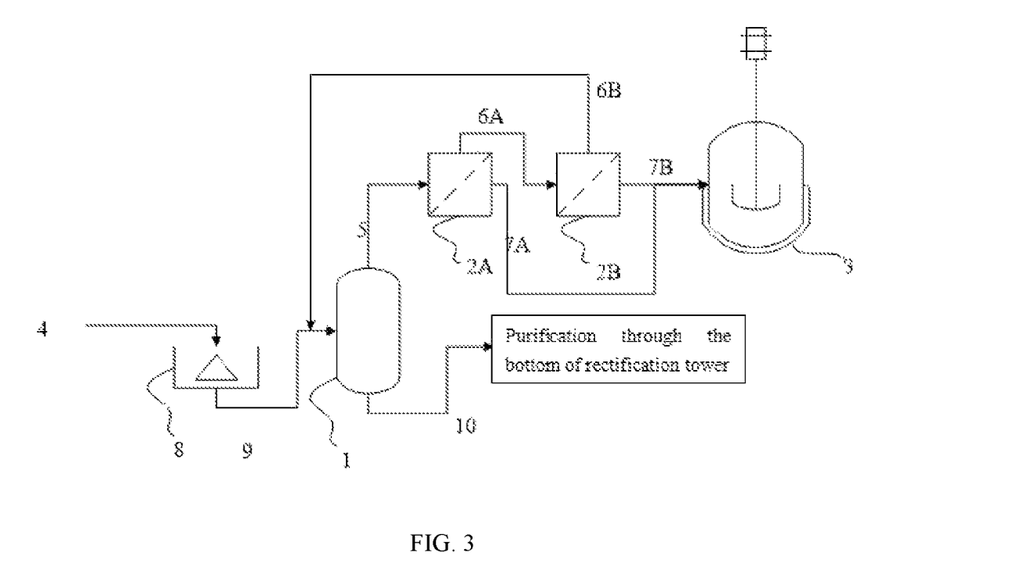
FIG. 3 is a flowchart of Example 3.

The process of a preparing method for extracting polyol from a fermentation process is shown in FIG. 3: the fermentation broth 4 for the desalination 8→the desalted solution 9 for the concentration 1→the concentrated solution 10 for purification through the bottom of the rectification tower while the steam condensate (including primary and secondary steam condensate) 5 for the first-stage reverse osmosis 2A→the penetrant of the first-stage reverse osmosis 7A for the fermentation 3 while the retentate of the first-stage reverse osmosis 6A for the second-stage reverse osmosis 2B→the penetrant of the second-stage reverse osmosis 7B for the fermentation 3 while the retentate of the second-stage reverse osmosis 6B for the concentration 1.

Example 4

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration, and after one-step desalination as the ion exchange desalination; wherein the polyol fermentation broth is fermented by *Klebsiella, Clostridium, Citrobacter, Lactobacillus,*

*Corynebacterium glutamicum* or *Escherichia coli*, or by the genetic engineering bacteria of these bacteria;

wherein the concentration of the polyol fermentation broth is one-step concentration as the MVR evaporative concentration;

wherein the reverse osmosis is three-stage reverse osmosis, which connects the reverse osmosis in series, and the retentate of the first-stage reverse osmosis is further filtered through the second-stage reverse osmosis, while the penetrant of the first-stage and second-stage reverse osmosis flows out; then the retentate of the second-stage reverse osmosis is further filtered through the third-stage reverse osmosis, and the retentate of the third-stage reverse osmosis flows back to the multi-effect evaporation for evaporative dehydration, while the penetrant of the third-stage reverse osmosis flows back to the raw material of the first-stage reverse osmosis.

Figure 4:
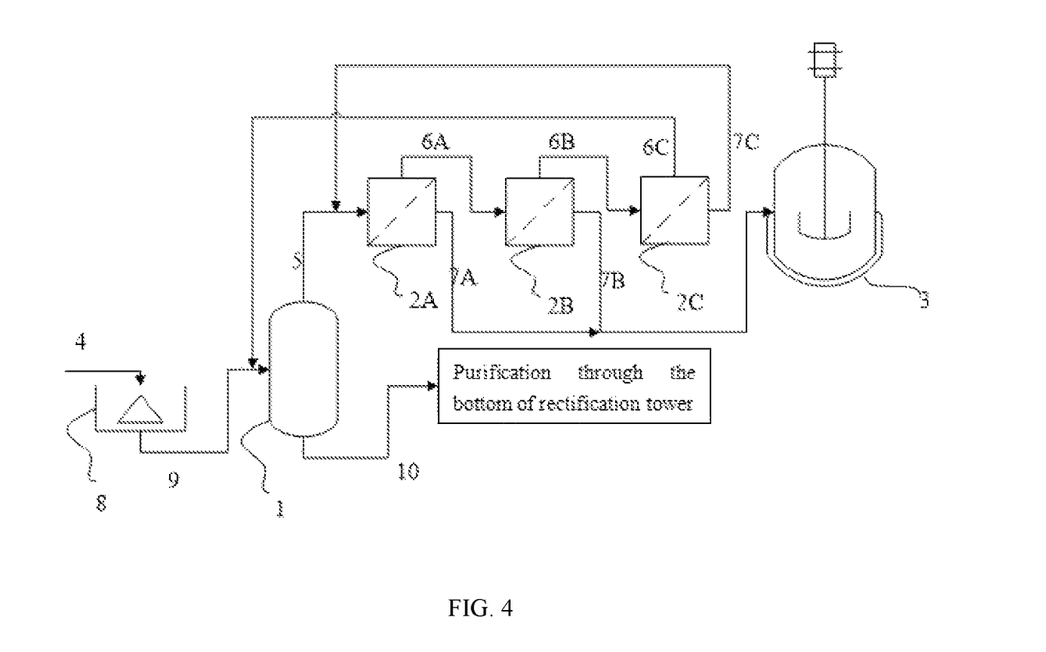
FIG. 4 is a flowchart of Example 4.

The process of a preparing method for extracting polyol from a fermentation process is shown in FIG. 4: the fermentation broth 4 for the desalination 8→the desalted solution 9 for the concentration 1→the concentrated solution 10 for purification through the bottom of the rectification tower while the steam condensate (including primary and secondary steam condensate) 5 for the first-stage reverse osmosis 2A→the penetrant of the first-stage reverse osmosis 7A for the fermentation 3 while the retentate of the first-stage reverse osmosis 6A for the second-stage reverse osmosis 2B→the penetrant of the second-stage reverse osmosis 7B for the fermentation 3 while the retentate of the second-stage reverse osmosis 6B for the third-stage reverse osmosis 2C→the penetrant of the third-stage reverse osmosis 7C for the first-stage reverse osmosis 2A while the retentate of the third-stage reverse osmosis 6C for the concentration 1.

Example 5

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration, and after one-step desalination as the concentrated crystallization desalination; wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria;

wherein the concentration of the polyol fermentation broth is one-step concentration as the multi-effect rectification;

wherein the reverse osmosis is three-stage reverse osmosis, which connects the reverse osmosis in series, and the penetrant of the first-stage reverse osmosis is further filtered through the second-stage reverse osmosis, and the penetrant of the second-stage reverse osmosis flows out, while the retentate of the first-stage reverse osmosis is further filtered through the third-stage reverse osmosis, and the retentate of the third-stage reverse osmosis flows back to the multi-effect evaporation for evaporative dehydration; then the retentate of the second-stage reverse osmosis and the penetrant of the third-stage reverse osmosis flows back to the raw material of the first-stage reverse osmosis.

Figure 5:
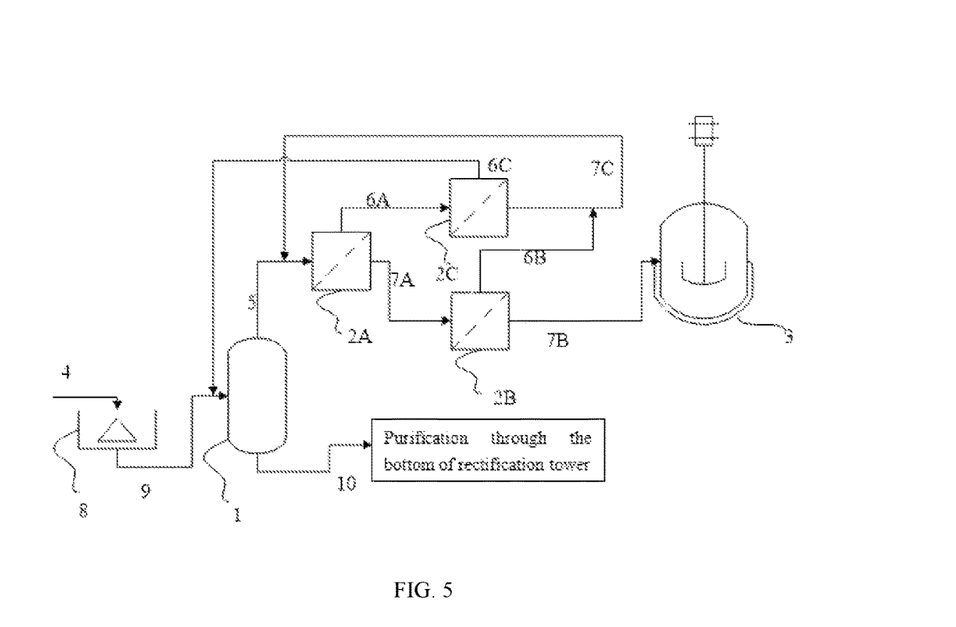
FIG. 5 is a flowchart of Example 5.

The process of a preparing method for extracting polyol from a fermentation process is shown in FIG. 5: the fermentation broth 4 for the desalination 8→the desalted solution 9 for the concentration 1→the concentrated solution 10 for purification through the bottom of the rectification tower while the steam condensate (including primary and secondary steam condensate) 5 for the first-stage reverse osmosis 2A→the penetrant of the first-stage reverse osmosis 7A for the second-stage reverse osmosis 2B while the retentate of the first-stage reverse osmosis 6A for the third-stage reverse osmosis 2C→the penetrant of the second-stage reverse osmosis 7B for the fermentation 3, the retentate of the second-stage reverse osmosis 6B for the first-stage reverse osmosis 2A, the penetrant of the third-stage reverse osmosis 7C for the first-stage reverse osmosis 2A, and the retentate of the third-stage reverse osmosis 6C for the concentration 1.

Example 6

A preparing method for extracting polyol from a fermentation process, which is characterized by rectifying and purifying PDO from a polyol fermentation broth after concentration to form a steam condensate, wherein the concentration is a evaporative dehydration; and filtering the steam condensate through a reverse osmosis membrane to form a concentrated solution, wherein the retentate of the reverse osmosis flows back to the evaporative dehydration, and the penetrant of the reverse osmosis can be reused as a fermentation ingredient, as cleaning water or for sewage treatment; and the water content of the concentrated solution after the evaporative dehydration is 5-25 wt %; and the yield of PDO is ≥99.5%; wherein the products of rectification and purification include PDO as well as BDO;

wherein the water content of the polyol fermentation broth is ≥80 wt %; wherein the polyol fermentation broth is the PDO fermentation broth after sterilization by filtration (a sterilization by microfiltration membrane filtration); wherein the polyol fermentation broth is fermented by *Klebsiella, Clostridium, Citrobacter, Lactobacillus, Corynebacterium glutamicum* or *Escherichia coli*, or by the genetic engineering bacteria of these bacteria;

wherein the concentration is two-step concentration, the concentrated solution is primary concentrated until the water content is 50-70 wt %; after 80-99 wt % salt is removed, the concentrated solution is secondary concentrated until the water content is 5-25 wt %; wherein the concentration is the multi-effect evaporative concentration, which refers to the steam of the former effect as the heat source of the latter effect, including a three-effect evaporation, a four-effect evaporation, a five-effect evaporation and a six-effect evaporation;

wherein the reverse osmosis is one-stage reverse osmosis.

Figure 6:
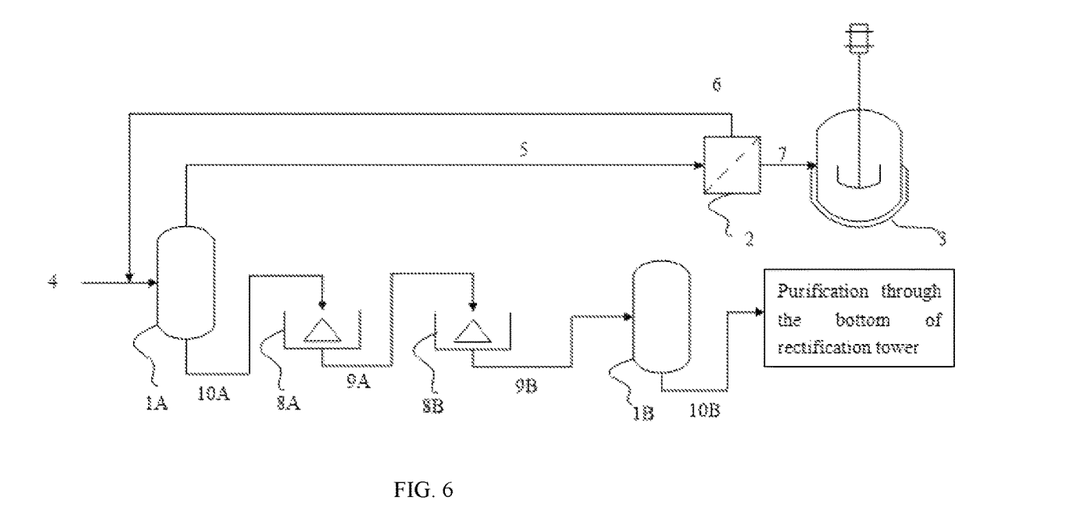
FIG. 6 is a flowchart of Example 6.

The process of a preparing method for extracting polyol from a fermentation process is shown in FIG. 6: the fermentation broth 4 for the primary concentration 1A→the primary concentrated solution 10A for the primary desalination 8A while the steam condensate (including primary and secondary steam condensate) 5 for the reverse osmosis 2→the primary desalted solution 9A for the secondary desalination 8B, the penetrant of the reverse osmosis 7 for the fermentation 3, and the retentate of the reverse osmosis 6 for the primary concentration 1A→the secondary desalted solution 9B for the secondary concentration 1B→the secondary concentrated solution 10B for purification through the bottom of the rectification tower.

Example 7

A preparing method for extracting polyol from a fermentation process, which is basically the same as Example 5, except that the polyol fermentation broth is the PDO fermentation broth after sterilization by filtration, and after multi-step desalination (combination of the concentrated crystallization desalination and the electrodialysis desalination).

Example 8

A preparing method for extracting polyol from a fermentation process, which is basically the same as Example 6, except that the concentration is three-step concentration. The concentrated solution is primary concentrated until the water content is 50-70 wt %; after 30-60 wt % salt is removed, the concentrated solution is secondary concentrated until the water content is 30-50 wt %; before the third step, the concentrated solution is desalted again until the total desalination rate is 80-99 wt %; then the concentrated solution is tertiary concentrated until the water content is 5-25 wt %.

Example 9

A preparing method for extracting polyol from a fermentation process, which is basically the same as Example 6, except that the sterilization by filtration is the sterilization by ultrafiltration.

Example 10

A preparing method for extracting polyol from a fermentation process, which is basically the same as Example 6, except that the sterilization by filtration is the sterilization by nanofiltration.

Example 11

A preparing method for extracting polyol from a fermentation process, which is basically the same as Example 6, except that the sterilization by filtration is a combination of the sterilization by microfiltration membrane filtration and the sterilization by ultrafiltration.

What is claimed is:

1. A preparing method for extracting polyol from a fermentation process, comprising rectifying and purifying PDO (1,3-propanediol) from a polyol fermentation broth after a concentration to form a steam condensate, wherein the concentration is an evaporative dehydration; and filtering the steam condensate through a reverse osmosis membrane to form a concentrated solution, wherein a retentate of a reverse osmosis flows back to the evaporative dehydration; wherein a water content of the concentrated solution after the evaporative dehydration is 5-25 wt %; wherein a yield of the PDO is ≥99.5%.

2. The preparing method of claim 1, wherein a water content of the polyol fermentation broth is ≥80 wt %; wherein the polyol fermentation broth is a PDO fermentation broth after a sterilization by a filtration, or the polyol fermentation broth is the PDO fermentation broth after the sterilization by the filtration and after a desalination.

3. The preparing method of claim 2, wherein the sterilization by the filtration is performed by at least one selected from the group consisting of a microfiltration membrane filtration, an ultrafiltration and a nanofiltration.

4. The preparing method of claim 2, wherein the desalination is at least one selected from the group consisting of a concentrated crystallization desalination, an electrodialysis desalination, a chromatographic separation desalination and an ion exchange desalination.

5. The preparing method of claim 2, wherein the desalination is a one-step desalination or a multi-step desalination.

6. The preparing method of claim 1, wherein the concentration is a one-step concentration or a stepwise concentration.

7. The preparing method of claim 6, wherein the stepwise concentration is a two-step concentration or a three-step concentration.

8. The preparing method of claim 7, wherein the two-step concentration comprises the following steps: performing a primary concentration on the concentrated solution is primary concentrated until the water content of the concentrated solution is 50-70 wt %; after 80-99 wt % of a salt is removed, performing a secondary concentration on the concentrated solution is secondary concentrated until the water content of the concentrated solution is 5-25 wt %.

9. The preparing method of claim 7, wherein the three-step concentration comprises the following steps: performing a primary concentration on the concentrated solution is primary concentrated until the water content of the concentrated solution is 50-70 wt %; after 30-60 wt % of a salt is removed, performing a secondary concentration on the concentrated solution is secondary concentrated until the water content of the concentrated solution is 30-50 wt %; before a third step of the three-step concentration, performing a desalination on the concentrated solution is desalted again until a total desalination rate of the concentrated solution is 80-99 wt %; then performing a tertiary concentration on the concentrated solution until the water content of the concentrated solution is 5-25 wt %.

10. The preparing method of claim 1, wherein the concentration is a multi-effect evaporative concentration, an MVR evaporative concentration or a multi-effect rectification.

11. The preparing method of claim 10, wherein the multi-effect evaporative concentration refers to a steam of a former effect as a heat source of a latter effect, and the multi-effect evaporative concentration comprises a three-effect evaporative concentration, a four-effect evaporative concentration, a five-effect evaporative concentration and a six-effect evaporative concentration.

12. The preparing method of claim 1, wherein the reverse osmosis is a one-stage reverse osmosis or a multi-stage reverse osmosis.

13. The preparing method of claim 12, wherein the multi-stage reverse osmosis refers to two or more stages of the reverse osmosis, the multi-stage reverse osmosis connects the reverse osmosis in series, and the retentate of a subsequent stage flows back to a previous stage while the retentate of the previous stage flows back to the evaporative dehydration.

14. The preparing method of claim 12, wherein the multi-stage reverse osmosis refers to two or more stages of the reverse osmosis, the multi-stage reverse osmosis connects the reverse osmosis in series; at the same time, the retentate of a first-stage reverse osmosis is further filtered through a second-stage reverse osmosis, while a penetrant of the first-stage reverse osmosis and the second-stage reverse osmosis flows out, and the retentate of the second-stage reverse osmosis flows back to a multi-effect evaporation for the evaporative dehydration.

15. The preparing method of claim 12, wherein the multi-stage reverse osmosis refers to two or more stages of the reverse osmosis, the multi-stage reverse osmosis connects the reverse osmosis in series; at the same time, the retentate of a first-stage reverse osmosis is further filtered through a second-stage reverse osmosis, while a penetrant of the first-stage reverse osmosis and the second-stage reverse osmosis flows out; then the retentate of the second-stage reverse osmosis is further filtered through a third-stage reverse osmosis, and the retentate of the third-stage reverse osmosis flows back to a multi-effect evaporation for the evaporative dehydration, while a penetrant of the third-stage reverse osmosis flows back to a raw material of the first-stage reverse osmosis.

16. The preparing method of claim 12, wherein the multi-stage reverse osmosis refers to two or more stages of the reverse osmosis, which the multi-stage reverse osmosis connects the reverse osmosis in series; at the same time, a penetrant of a first-stage reverse osmosis is further filtered through a second-stage reverse osmosis, and a penetrant of the second-stage reverse osmosis flows out, while the retentate of the first-stage reverse osmosis is further filtered through a third-stage reverse osmosis, and the retentate of the third-stage reverse osmosis flows back to a multi-effect evaporation for the evaporative dehydration; then the retentate of the second-stage reverse osmosis and a penetrant of the third-stage reverse osmosis flows back to a raw material of the first-stage reverse osmosis.

17. The preparing method of claim 1, wherein products of a rectification and a purification comprise the PDO and BDO (2,3-butanediol).

18. The preparing method of claim 1, wherein the polyol fermentation broth is fermented by *Klebsiella, Clostridium, Citrobacter, Lactobacillus, Corynebacterium glutamicum* or *Escherichia coli*, or by genetic engineering bacteria of the *Klebsiella*, the *Clostridium*, the *Citrobacter*, the *Lactobacillus*, the *Corynebacterium glutamicum* or the *Escherichia coli*.

19. The preparing method of claim 1, wherein a penetrant of the reverse osmosis is reused as a fermentation ingredient, as cleaning water or fora sewage treatment.

20. The preparing method of claim 6, wherein the concentration is a multi-effect evaporative concentration, an MVR evaporative concentration or a multi-effect rectification.

21. The preparing method of claim 7, wherein the concentration is a multi-effect evaporative concentration, an MVR evaporative concentration or a multi-effect rectification.

22. The preparing method of claim 8, wherein the concentration is a multi-effect evaporative concentration, an MVR evaporative concentration or a multi-effect rectification.

23. The preparing method of claim 9, wherein the concentration is a multi-effect evaporative concentration, an MVR evaporative concentration or a multi-effect rectification.

* * * * *